(12) United States Patent
Bradley

(10) Patent No.: US 7,020,947 B2
(45) Date of Patent: Apr. 4, 2006

(54) METAL WIRE WITH FILAMENTS FOR BIOMEDICAL APPLICATIONS

(75) Inventor: David Jeurgens Bradley, Fort Wayne, IN (US)

(73) Assignee: Fort Wayne Metals Research Products Corporation, Fort Wayne, IN (US)

( * ) Notice: Subject to any disclaimer, the term of this patent is extended or adjusted under 35 U.S.C. 154(b) by 25 days.

(21) Appl. No.: 10/668,766

(22) Filed: Sep. 23, 2003

(65) Prior Publication Data
US 2005/0060861 A1   Mar. 24, 2005

(51) Int. Cl.
*B21D 39/00* (2006.01)
*A61F 2/06* (2006.01)

(52) U.S. Cl. ............. 29/515; 29/516; 29/458; 623/1.11; 623/1.15; 623/1.39

(58) Field of Classification Search ............ 29/458, 29/515, 516, 517, 401.1, 447, 419, 599; 623/1.11, 1.15, 1.39, 1.38, 1.2, 1.22, 23.7, 623/23.75; 606/194, 195
See application file for complete search history.

(56) References Cited

U.S. PATENT DOCUMENTS

| | | | |
|---|---|---|---|
| 2,050,298 A * | 8/1936 | Everett .................... | 139/387 R |
| 3,205,692 A | 9/1965 | Kemppinen et al. .......... | 72/264 |
| 3,591,915 A | 7/1971 | Roberts et al. .............. | 29/417 |
| 3,618,614 A | 11/1971 | Flynn ........................ | 128/348 |
| 3,882,587 A | 5/1975 | Schneider et al. ........ | 29/419 R |
| 4,065,046 A | 12/1977 | Roberts et al. ............. | 228/156 |
| 4,094,060 A * | 6/1978 | Madsen et al. ............... | 29/599 |
| 4,242,536 A * | 12/1980 | Young .................... | 174/125.1 |
| 4,959,279 A * | 9/1990 | Tanaka et al. .............. | 428/660 |
| 5,034,857 A * | 7/1991 | Wong ........................ | 361/509 |
| 5,047,050 A | 9/1991 | Arpesani ....................... | 623/1 |
| 5,289,831 A | 3/1994 | Bosley ...................... | 128/899 |
| 5,320,100 A | 6/1994 | Herweck et al. ........... | 128/654 |
| 5,447,672 A | 9/1995 | O'Neil ....................... | 264/166 |
| 5,607,442 A | 3/1997 | Fischell et al. ............. | 606/191 |
| 5,628,787 A * | 5/1997 | Mayer ....................... | 623/1.15 |
| 5,709,021 A | 1/1998 | DiCello et al. ............... | 29/423 |
| 5,725,572 A | 3/1998 | Lam et al. ..................... | 623/1 |
| 5,735,897 A | 4/1998 | Buirge ......................... | 623/12 |
| 5,759,174 A | 6/1998 | Fischell et al. ............... | 604/96 |
| 5,873,904 A | 2/1999 | Ragheb et al. ................ | 623/1 |

(Continued)

FOREIGN PATENT DOCUMENTS

EP        1 334 701        8/2003

*Primary Examiner*—Marc Jimenez
(74) *Attorney, Agent, or Firm*—Baker & Daniels LLP

(57) ABSTRACT

A method for constructing a metal wire with embedded filaments or cavities therein for biomedical applications. The method includes first drilling nonconcentric apertures in a symmetrical pattern in a metal rod and then embedding filaments in the apertures. The metal rod is then drawn and thermally-treated to form a metal wire with embedded filaments therein. The filaments may advantageously provide fatigue resistance, radiopacity, and electrical conductance to the metal wire. The method optionally provides an additional step for withdrawing or removing the filaments using various methods to create cavities for cavity access within the metal wire. The metal wire may be finished to provide access to the cavities or filaments embedded therein. The cavities may then be filled with a therapeutic drug for elution inside the human body or used for passage of body fluids. An optional biocompatible coating may be disposed around the metal wire to prevent escape of the therapeutic drug before insertion into the human body. The cavities may also be filled with different materials as compared to the original filaments.

13 Claims, 2 Drawing Sheets

U.S. PATENT DOCUMENTS

| | | |
|---|---|---|
| 5,873,907 A | 2/1999 | Frantzen .......................... 623/1 |
| 5,890,272 A | 4/1999 | Liberman et al. .......... 29/419.1 |
| 5,891,108 A | 4/1999 | Leone et al. ................. 604/264 |
| 5,902,266 A | 5/1999 | Leone et al. ................... 604/53 |
| 6,112,395 A | 9/2000 | Quick et al. ............... 29/419.1 |
| 6,170,147 B1 * | 1/2001 | Yamada et al. ............... 29/599 |
| 6,190,303 B1 | 2/2001 | Glenn et al. .................... 600/3 |
| 6,200,338 B1 | 3/2001 | Solomon et al. ........... 623/1.34 |
| 6,203,732 B1 | 3/2001 | Clubb et al. ................... 264/81 |
| 6,206,915 B1 | 3/2001 | Fagan et al. ................ 623/1.42 |
| 6,240,616 B1 | 6/2001 | Yan ........................... 29/527.2 |
| 6,364,902 B1 | 4/2002 | Dickenson et al. ........ 623/1.15 |
| 6,471,721 B1 | 10/2002 | Dang ........................ 623/1.34 |
| 6,497,029 B1 | 12/2002 | Quick et al. ............... 29/419.1 |
| 6,652,582 B1 * | 11/2003 | Stinson ..................... 623/1.39 |
| 2003/0074779 A1 * | 4/2003 | Wong .......................... 29/599 |

* cited by examiner

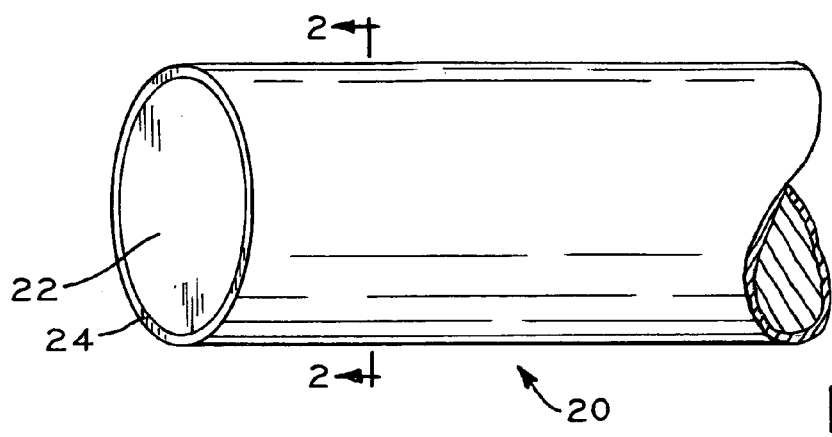
FIG_1
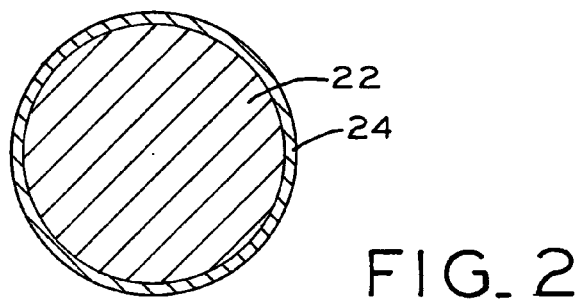
FIG_2
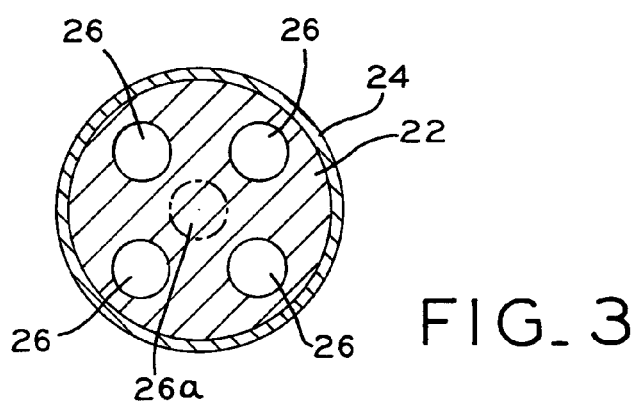
FIG_3
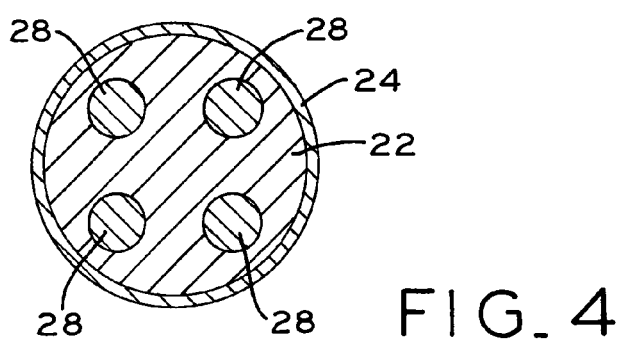
FIG_4

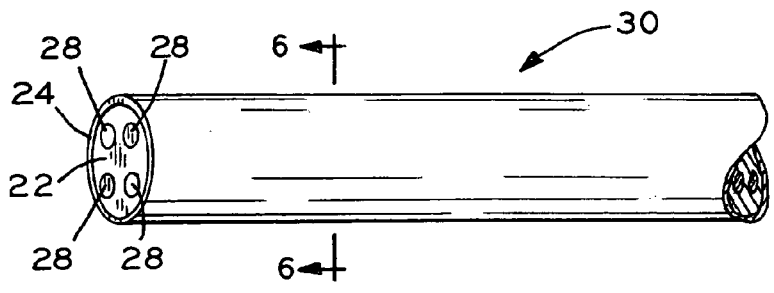
FIG_5
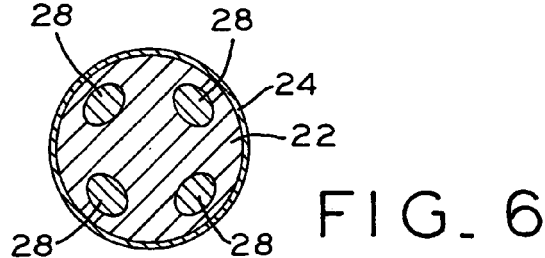
FIG_6
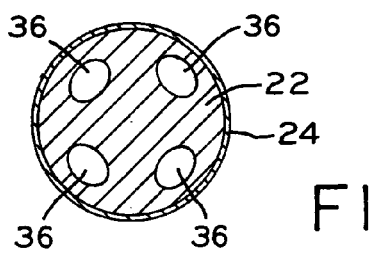
FIG_7
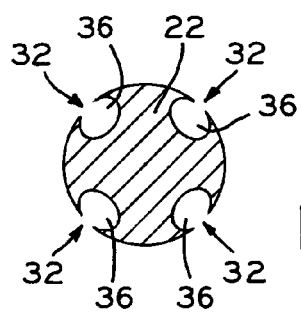
FIG_8
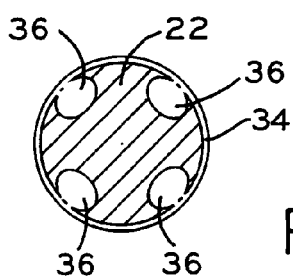
FIG_9

METAL WIRE WITH FILAMENTS FOR BIOMEDICAL APPLICATIONS

BACKGROUND

The present invention relates generally to biomedical device components for use in the human body. More particularly, the invention relates to a method for constructing metal wire with embedded filaments or cavities for biomedical applications.

In the field of biomedical device components, it is important to have biocompatible devices which can be implanted into a human body for various purposes. Biomedical implant devices are well-known in the art, as described in the following U.S. Pat. Nos. 6,364,902; 6,206,915; 6,203,732; 6,200,338; 6,190,303; 5,873,907; 5,873,904; 5,759,174; 5,735,897; 5,725,572; 5,628,787; 5,607,442; 5,320,100; 5,289,831; 5,047,050; and 3,618,614. Biomedical implant devices have numerous applications and may need to be very small in size depending on the application. It may be beneficial to allow placement of an additional material inside or on the outside surface of the biomedical device. In one instance, a biomedical device may be a metal wire having a concentric core with a secondary material, such as platinum, located therein. To obtain the entire benefit of the device, such as, i.e., radiopacity or fatigue resistance, however, a large amount of the secondary material is needed to permeate the surrounding material of the metal wire. The amount of secondary material required for various applications raises the cost of the biomedical device considerably in some instances. If it were possible to position the secondary material closer to the surface of the metal wire, there would be less surrounding material of the metal wire to permeate, thereby increasing the effectiveness and decreasing the cost of the biomedical device.

SUMMARY OF THE INVENTION

The present invention provides an improved method for constructing a metal wire with embedded filaments or cavities therein for biomedical applications. The method entails first drilling nonconcentric apertures in a symmetrical pattern in a metal rod and then embedding filaments in the apertures. The metal rod is then drawn and thermally-treated to form a metal wire with embedded filaments therein. The filaments may advantageously provide fatigue resistance, structural support, radiopacity, a biological therapeutic effect and electrical conductance to the metal wire. The metal wire may be placed into a human body for various biomedical applications. In another embodiment, the present invention optionally provides an additional step for withdrawing or removing the filaments using various methods to create cavities for cavity access within the metal wire. In another alternative embodiment of the present invention, the metal wire may be finished to provide avenues of exposure to the cavities or filaments embedded therein. The cavities may then be filled with a pharmaceutical drug or metal oxide, ceramic oxide, particulate carrier, or polymer for carrying such drug for elution inside the human body or may be used for passage of body fluids. An optional biocompatible pharmaceutical drug or oxide polymer or metal ion for carrying such drug may be disposed around the metal wire to create a further reservoir for the therapeutic drug. The cavities may also be filled with different materials as compared to the original filaments to provide various advantages.

The process of the present invention advantageously provides a method of constructing a metal wire which has enhanced fatigue resistance.

Another advantage of the process of the present invention is that the process provides for the removal of the embedded filaments, thereby creating cavities into which therapeutic drugs may be placed for medicinal purposes in a human body or which may be used for passage of body fluids.

A further advantage of the process of the present invention is that the process provides for the placement of radiopaque materials embedded in the metal wire, thereby allowing physicians to easily locate an implant once placed inside a human body.

The process of the present invention also advantageously provides a process for making a biocompatible implant with electrical conductance capabilities to be used in various heart procedures including cauterizing blood vessels or providing a pattern of lesions on heart muscle.

A yet further advantage is that the inventive process provides for the nonconcentric and symmetrical filaments or cavities to be positioned closer to the surface of the metal wire, thereby reducing the amount of surrounding material to permeate.

In one embodiment, the present invention provides a method of making a metal wire including the steps of drilling apertures in a parent material; filling the apertures with filaments; and repeatedly drawing and thermally-treating the parent material with the filaments embedded therein to form the metal wire.

In another embodiment, the present invention provides a method of making a metal wire comprising the steps of drilling apertures in a parent material; filling the apertures with filaments; repeatedly drawing and thermally-treating the parent material with the filaments embedded therein to form the metal wire; and removing the filaments from the parent material to form cavities within the metal wire.

In a further embodiment, the present invention provides a method of making a metal wire comprising the steps of drilling apertures in a parent material; filling the apertures with filaments; repeatedly drawing and thermally-treating the parent material with the filaments embedded therein to form the metal wire; removing the filaments from the parent material to form cavities within the metal wire; and finishing the metal wire to provide an avenue of exposure to the cavities.

In a still further embodiment, the present invention provides a method of making a metal wire comprising the steps of drilling apertures in a parent material; filling the apertures with filaments; repeatedly drawing and thermally-treating the parent material with the filaments embedded therein to form the metal wire; removing the filaments from the parent material to form cavities within the metal wire; filling the cavities with a filler material; and finishing the metal wire to provide an avenue of exposure to the filler material.

In yet another alternative embodiment, the present invention provides a machine for manufacturing a metal wire including means for drilling apertures in a parent material; means for filling the apertures with filaments; and means for repeatedly drawing and thermally-treating the parent material with the filaments embedded therein to form the metal wire.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is a partial plan view showing a metal rod encapsulated with a coating prior to the initial step of the present invention;

FIG. 2 is a cross-sectional view of the metal rod of FIG. 1;

FIG. 3 is a cross-sectional view of the metal rod of FIG. 1 showing the result of the initial step of the method of the present invention;

FIG. 4 is a cross-sectional view of the metal rod of FIG. 1 showing the result of an additional step of the method of the present invention;

FIG. 5 is a partial plan view illustrating another step of the method of the present invention;

FIG. 6 is a cross-sectional view of the metal wire of FIG. 5;

FIG. 7 is a cross-sectional view of the metal wire of FIG. 5 showing an additional step of the method of the present invention;

FIG. 8 is a cross-sectional view of the metal wire of FIG. 5 illustrating a further step of the method of the present invention; and FIG. 9 is a cross-sectional view of the metal wire of FIG. 5 showing another step of the method of the present invention.

Corresponding reference characters indicate corresponding parts throughout the several views. The exemplifications set out herein illustrate several exemplary embodiments of the invention and such exemplifications are not to be construed as limiting the scope of the invention in any manner.

DETAILED DESCRIPTION

Referring now to the drawings and in particular FIG. 1, rod 20 is provided and includes parent material 22. Coating 24 is optionally provided to encapsulate parent material 22 and may be metal, ceramic, or plastic (i.e., Ethyl Tetra Fluoride (ETFE) or Poly Tetra Fluoride (PTFE)). Parent material 22 could be a biocompatible material such as a cobalt-based alloy. One such cobalt-based alloy is ASTM F 562. Alternatively, parent material 22 could be a stainless steel, super-alloy, or reactive alloy such as ASTM F 899, ASTM F 90 or ASTM F 590. FIG. 2 shows a cross-section of rod 20 as illustrated in FIG. 1 and, in an exemplary embodiment, rod 20 may be approximately 1 to 2 inches in diameter. However, rod 20 initially may be of any suitable size to fit manufacturing tolerances and needs.

The result of the initial step of the process of the present invention is shown in FIG. 3. Apertures or holes 26 are created using conventional methods. Holes 26 may be electro-polished thereafter. Apertures 26 may be advantageously nonconcentric and extend throughout the length of rod 20. Apertures 26 may be advantageously aligned symmetrically around the center of rod 20 to provide for congruency of shape of apertures 26 during a drawing process, as described below. Although illustrated as circular in shape in FIG. 3, apertures 26 may be any shape, alignment, or number necessary for a desired application. Central aperture 26a is optionally provided, the advantage of which will be described with reference to FIG. 6.

Once apertures 26 are provided in parent material 22, filaments 28 are inserted thereinto, as shown in FIG. 4. Filaments 28 may include various materials. For instance, filaments 28 could be made of platinum, or a similar radiopaque material, to advantageously provide radiopacity to the finished product. In another embodiment, filaments 28 could include fatigue resistant alloys, such as ASTM F 562 or ASTM F 590, to advantageously provide fatigue resistance. In another embodiment, filaments 28 could include alloys capable of undergoing a phase or property change as a result of a natural or artificial outside stimulus such as irradiation, thermal activation or acoustic stimulation. In yet another embodiment, filaments 28 could include a sensitized stainless steel or a mild steel to allow for acid bath removal of filaments 28 at a later time. In yet another embodiment, filament 28 could be a magnesium based alloy and thermally oxidized to allow for removal of filaments 28 at a later time. Additionally, filaments 28 could be silver, nitinol (an alloy made of 50% nickel and 50% titanium), or any other suitable metallic material desired for the applicable situation.

Rod 20 with filaments 28 embedded therein is then subjected to a drawing and thermal-treatment process, the result of which is shown in FIG. 5. As mentioned previously, rod 20 can initially be approximately 1 to 2 inches in diameter. The result in FIG. 5 is metal wire 30 which may be less than 1/1000 of an inch in diameter. Metal wire 30 is the result of a cold-working process which may be accomplished using conventional drawing methods to draw rod 20. After drawing, there is a need to restore the properties of the metal to facilitate continued drawing. To facilitate further drawing, annealing, or thermally-treating of rod 20 is necessary in order for the grains of rod 20 to reform and to allow rod 20 to become more ductile and softer. The thermal-treatment stage is an intermittent stage in the process. The result shown in FIG. 5 is thus the result of a repeated procedure of first drawing rod 20 and then thermally-treating rod 20 until rod 20 is drawn to the size desired for metal wire 30.

Metal wire 30 is shown in cross-section in FIG. 6 and includes filaments 28, parent material 22 and, optionally, coating 24. Filaments 28 in FIG. 6 are shown as slightly oval-shaped as compared to being generally circular in FIG. 4. This deformation is caused by the drawing process and filaments 28 will be increasingly oval-shaped as the strength of filaments 28 decreases with respect to the strength of parent material 22. Thus, if filaments 28 are extremely hard metallic materials, the deformation will be slight. However, if filaments 28 are soft metallic materials, the deformation will be greater. As mentioned above with respect to FIG. 3, aperture 26a could be provided before the drawing process and filled with filament 28a (not shown) to effect the amount of distortion of filaments 28.

In a further embodiment of the present invention, the result of which is shown in FIG. 7, filaments 28 are withdrawn or removed from parent material 22 and cavities 36 remain. Filaments 28 may be removed through a number of different processes. For instance, one such removal process would include placing a section of metal wire 30 into an acid bath that would attack the embedded material and remove filament 28, but would not effect parent material 22, thereby leaving cavities 36. Filaments 28 may also be removed from parent material 22 via a biodegradable or thermally activated corrosive attack process, whereby filaments 28 were leached out to leave cavities 36 in parent material 22. Filaments 28 may also be removed from parent material 22 via a micro or nano machining process, whereby filaments 28 are mechanically removed to leave cavities 36 in parent material 22.

Cavities 36 may be filled with a different material than filaments 28. In one exemplary embodiment, cavities 36 may be filled with a therapeutic drug (not shown). The therapeutic drug can then be advantageously used for elution within the human body after implantation of small segments of metal wire 30 therein. The drug eluting capabilities of the present invention are less traumatic for a patient because metal wire 30 slowly elutes drugs into the human body. For example, if a patient were treated by application of a drug from the outside of the body, such as by injection, the repeated needle bursts of drug therapy could cause bad side effects. The drug eluting capabilities of the present invention advantageously minimizes the side effects of receiving drug therapy because there is no need for repetition of drug therapy. In addition therapeutic drugs can assist the human or animal body with microbial control, antirestenosis behavior, thrombosis prevention, and encrustation resulting from bodily salt crystals. Once metal wire 30 is placed in the body, there is a reduced need to provide outside drug therapy. In another embodiment, cavities 36 may be used for passage of body fluids in a human body.

To take full advantage of the inherent properties of the filler material in cavities 36 or filaments 28, a process of finishing metal wire 30 is provided to reduce the diameter of metal wire 30 and provide avenues of exposure 32, the result of which is shown in FIG. 8. FIG. 8 only shows the finishing step after filaments 28 have been removed, but the finishing step may be done before filaments 28 are removed to provide avenues of exposure 32 to filaments 28. When coating 24 is removed and parent material 22 is reduced in diameter to advantageously provide filaments 28 or cavities 36 closer proximity to the edge of metal wire 30, there is less parent material 22 to permeate, thereby reducing the amount of material necessary for filaments 28 and providing easier access to cavities 36. This reduces cost and labor for the production of metal wire 30. The finishing process to reduce the diameter of metal wire 30 may consist of a number of processes including chemical etching, thermal processing, grinding, laser processing, shot-peening, electro-polishing, or any other suitable abrasion-type activity. The finishing process could also include drawing die surface modification wherein a die has a rough surface to peel or scratch the material exposed to the die. In all embodiments, however, the finishing will provide avenues of exposure 32, as shown in FIG. 8. Avenues of exposure 32 advantageously provide an avenue for the filler material in cavities 36 or filaments 28 to reach the perimeter of metal wire 30. In an exemplary embodiment, when a therapeutic drug is placed in cavities 36 and metal wire 30 has been finished to include avenues of exposure 32, drug elution is more effective once metal wire 30 is placed in a human body because the drug may easily exit metal wire 30 via avenues of exposure 32. In a further embodiment, biocompatible finish coating 34, as shown in FIG. 9, encapsulates metal wire 30 to prevent leakage of a therapeutic drug from cavity 36 before insertion into a human body and then, once placed in a human body, to allow escape of the therapeutic drugs from cavities 36. The biocompatible finishing coating could be a metal oxide, ceramic oxide, particulate carrier, or polymer such as N-isopropylacrylamide (NiPAAm) and N-tert-butylacrylamide (NtBAAm) co-polymer or poly vinyl acetate. In another alternative embodiment, when filaments 28 are made of a radiopaque material, such as platinum, or radiopaque material is placed in cavities 36, the increased radiopacity of metal wire 30 advantageously provides easier location of metal wire 30 inside a human body. In a still further embodiment when filament 28 is a strong material or a strong material is placed in cavities 36, the fatigue resistance of metal wire 30 is increased because there is stronger material on the outside of metal wire 30. Examples of such materials would be ASTM F 562 or ASTM F 590.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of making a wire, comprising the steps of:
   drilling a plurality of apertures in a parent material;
   filling at least one said apertures with a filament;
   repeatedly drawing and thermally-treating said parent material with said filaments embedded therein to form said wire; and
   opening said apertures to the outside circumference of said wire whereby a grooved wire is formed.

2. The method of claim 1, wherein said filaments comprise metallic materials.

3. The method of claim 1, further comprising the step of covering said wire with a biocompatible finish coating.

4. A method of making a wire, comprising the steps of:
   drilling a plurality of apertures in a parent material;
   filling at least one said aperture with a filament;
   repeatedly drawing and thermally-treating said parent material with said filaments embedded therein to form said wire; and
   removing said filament from said parent material to form a cavity within said wire whereby a wire with longitudinal grooves therein is formed.

5. The method of claim 4, wherein said filaments comprise metallic materials.

6. The method of claim 4, further comprising the step of covering said wire with a biocompatible finish coating.

7. A method of making a wire, comprising the steps of:
   drilling a plurality of apertures in a parent material;
   filling said apertures with filaments;
   repeatedly drawing and thermally-treating said parent material with said filaments embedded therein to form said wire;
   removing said filaments from said parent material to form cavities within said wire; and
   finishing said wire to open said cavities to the outside circumference of said wire whereby a grooved wire is formed.

8. The method of claim 7, wherein said filaments comprise metallic materials.

9. The method of claim 7, further comprising the step of covering said wire with a biocompatible finish coating.

10. A method of making a wire, comprising the steps of:
    drilling a plurality of apertures in a parent material;
    filling said apertures with filaments;
    repeatedly drawing and thermally-treating said parent material with said filaments embedded therein to form said wire;
    removing said filaments from said parent material to form cavities within said wire;
    finishing said wire to provide access to each of said cavities from the outside of said wire; and
    filling said cavities with a filler material whereby a wire with longitudinal filled grooves is formed.

11. The method of claim 10 wherein said filaments comprise metallic materials.

12. The method of claim 10, further comprising the step of covering said wire with a biocompatible finish coating of metal oxide, ceramic oxide, particulate carrier, or polymer.

13. The method of claim 10, wherein said filler material comprises metallic material.

* * * * *